United States Patent [19]

Lee

[11] 4,289,711
[45] Sep. 15, 1981

[54] ESTER SYNTHESIS

[75] Inventor: Grahame R. Lee, Strood, England

[73] Assignee: Burroughs Wellcome Co., Research Triangle Park, N.C.

[21] Appl. No.: 720,347

[22] Filed: Sep. 3, 1976

[30] Foreign Application Priority Data

Sep. 5, 1975 [GB] United Kingdom ............... 36688/75
Aug. 4, 1976 [GB] United Kingdom ............... 32483/76

[51] Int. Cl.³ .......................................... C07C 143/68
[52] U.S. Cl. ........................... 260/456 P; 260/326 A; 260/326 S; 260/347.2; 260/347.4; 260/464; 260/465 D; 560/124; 560/226; 560/227; 560/228
[58] Field of Search .......... 260/456 R, 456 P, 468 H, 260/347.4, 347.2, 464, 465 D, 326 A, 326 S; 560/124, 226, 227, 228

[56] References Cited

U.S. PATENT DOCUMENTS

| | | | |
|---|---|---|---|
| 3,397,223 | 8/1968 | Payne | 260/464 |
| 3,728,372 | 4/1973 | Siddall | 260/456 R |
| 3,792,079 | 2/1974 | D'Orazio | 260/456 P |
| 3,922,269 | 11/1975 | Elliott et al. | 260/468 H |
| 3,969,393 | 7/1976 | Mizutani et al. | 260/468 H |
| 3,979,519 | 9/1976 | Punja | 260/468 H |

FOREIGN PATENT DOCUMENTS 1413491 11/1975 United Kingdom ........... 260/468 H

OTHER PUBLICATIONS

Brown, Ind. Eng. Chem., 36, 785, (1944).
Payne, J. Org. Chem., 32, 3351, (1967).
Matsui et al., Agr. Biol. Chem., 28, 456, (1964).

Primary Examiner—Nicky Chan
Attorney, Agent, or Firm—Donald Brown

[57] ABSTRACT

A novel process is described for the preparation of compounds of formula

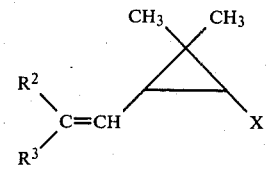

wherein $R^2$ and $R^3$ are each chloro or bromo; X is carboxyl, nitrile, optionally substituted carbonamide, carbonyl halide or an ester group. Those compounds wherein X is an appropriate ester group —COOB where B is an aryl group such as m-phenoxybenzyl are known insecticides; compounds where X is other than —COOB may be suitably converted thereto.

The novel process consists of a series of steps from the corresponding acetyl compound of formula

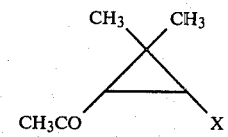

which comprises halogenation, reduction, esterification and finally elimination reactions.

4 Claims, No Drawings

ESTER SYNTHESIS

This invention relates to a novel method of making known vinylcyclopropane carboxylate esters, the esters so prepared, and to certain novel intermediates useful in the method and their synthesis.

British Patent Specification No. 1,413,491 discloses compounds of the general formula (A):

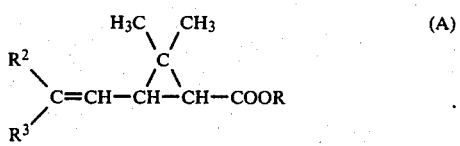

wherein, inter alia, $R^2$ and $R^3$ are each halo and R is alkyl, hydrogen (or a salt or acid halide derivative of the acid), as intermediates for the synthesis of insecticidal esters of formula (I) wherein B is a cyclic residue as further defined and illustrated hereinafter, and $R^2$ and $R^3$ are each halo. In this specification halo means chloro or bromo. In the abovementioned patent specification these insecticidal esters are described as having promising activity against a great variety of arthropod pests.

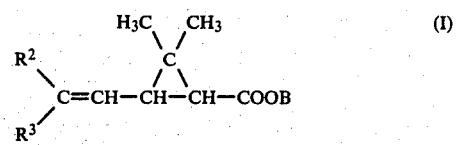

One method of synthesis involves the reaction of 1,1-dihalo-4-methyl-1,3-pentadiene with an alkyl diazoacetate. This synthesis is however hazardous in view of the toxicity and explosive character of the diazoacetates.

Another method of synthesis involves a Wittig synthesis according to the following equation:

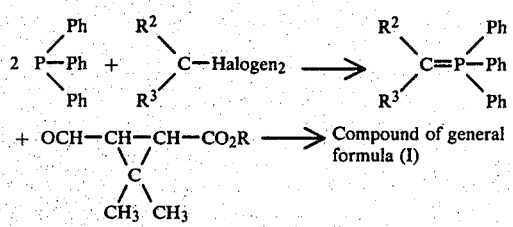

wherein R, $R^2$ and $R^3$ have the same meaning as in formula (A), but unfortunately the synthesis leads to the formation of an undesirable impurity and ring opening (J. Chem. Soc. 2470, 1974 and Supplement Publication No. SUP 2113 at page 9).

It has now been found that the esters of formula (I) can be conveniently made by the synthetic route outlined below in Scheme A.

SCHEME A

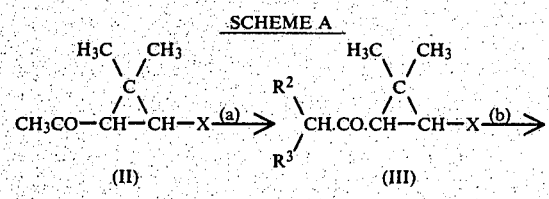

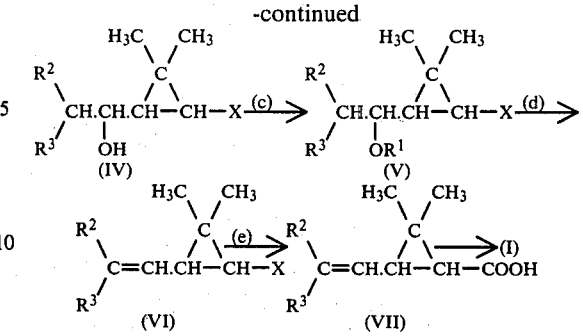

This route involves the formation of compounds of formula (II) to (VII) wherein each of $R^2$ and $R^3$ is chloro or bromo and X is nitrile, carboxyl, carbonamide ($-CONH_2$), carbonamide substituted by one or two alkyl groups each having from 1 to 4 carbon atoms, carbonylchloride, carbonylbromide, or an ester group $-COOM$ wherein M is lower alkyl, aralkyl or aryl. In the meaning of M, suitable lower alkyl groups have 1 to 6 carbon atoms, for example hexyl, pentyl, butyl, propyl or methyl but preferably ethyl; suitable aralkyl groups comprise a lower alkylene radical having 1 to 3 carbon atoms and a benzene ring which may be further substituted by lower alkyl or halo, for example benzyl or phenethyl; and suitable aryl groups are of formula (B) as hereinafter defined.

In the method of the present invention it has been surprisingly found that the dihalo compounds (III) can be readily formed by halogenation of the acetyl compounds (II) without contamination with the monohalo compounds or formation of the corresponding trihalo compounds. Moreover, it was found possible to convert the secondary alcohols (IV) to the desired vinyl compounds (VI) by first forming an ester (V), wherein $R^1O$ is a leaving group, and eliminating in step (d) said group $R^1O$ and a hydrogen so as to form an ethylenic bond in a compound of formula (VI) without opening the cyclopropane ring. The acid $R^1OH$ which is provided by the elimination step may then be reused to form further ester (V).

Chlorination of the acetyl compounds (II) is preferably carried out using sulphuryl chloride. The reaction may be carried out at from 0° C. up to the reflux temperature of the reaction mixture, and is preferably in the range of from 0° to 50° C. Desirably the sulphuryl chloride is used in molar excess, for example 2 to 10 times conveniently 2 to 4 times the molar equivalent of an acetyl compound (II). The reaction proceeds readily in the absence of solvent although if desired one may be used, any inert solvent which is compatible with the reactants may be used for example a halogenated hydrocarbon such as carbon tetrachloride or methylene chloride.

Chlorination may also be effected using molecular chlorine in the presence of a catalyst, such as a peroxide (eg. benzoyl peroxide) or light, particularly untra-violet light. Although the reaction may proceed without a solvent, it is convenient to use an inert solvent such as a halogenated hydrocarbon which will not itself be chlorinated in the course of the reaction. A suitable temperature for effecting the reaction is in the range of from 0° to 50° C. for example from 0° to 40° C., and the reaction is conveniently carried out at room temperature.

Alternatively, chlorination with molecular chlorine proceeds in the absence of a catalyst if carbontetrachloride is used as a solvent. The reaction is conveniently effected at from 0° to 50° C., for example at room temperature.

Bromination may be carried out using methods analogous to those suitable for effecting chlorination, for example in an inert solvent in the presence of a catalyst, or alternatively without a catalyst if ether is used as the solvent. A suitable temperature for this reaction being from 0° to 50° C. for example at room temperature.

The reduction (b) of the dihalo compounds (III) to the hydroxy compounds (IV) may be effected by any method for the reduction of ketones to secondary alcohols. Such methods include the use of an alkali metal with an alkanol such as methanol, ethanol, a propanol or a butanol, preferably sodium is used in the presence of ethanol; sodium, potassium or aluminium amalgam and water; the Ponndorf method using an alkanol and an aluminium alkoxide, such as aluminium isopropoxide and isopropanol; and catalytic hydrogenation with for example a nickel catalyst, suitable solvents for this reaction include alkanols and acetic acid. Preferably reduction is achieved using a hydride, for example an alkali metal borohydride, such as sodium borohydride; a solvent is not essential to the reaction but preferably water or an alkanol is used. An alkanol, and the corresponding alkoxide, when used in this specification has 1 to 6, preferably 1 to 4 carbon atoms. In general, the above-mentioned reduction reactions will be carried out substantially as known to those skilled in the art, see for example, Rodd's Chemistry of Carbon Compounds, Second Edition, edited by S. Coffey, Elsevier Publishing Company (1965) 1b, p. 7 and 1c, p. 60.

In step (c), an alcohol (IV) may be converted to its ester (V) by reaction with the acid $R^1.OH$ or a reactive derivative thereof such as the acid chloride, acid bromide or acid anhydride; although not essential, the reaction is conveniently effected in the presence of an inert solvent such as a halogenated hydrocarbon or ether, but preferably a basic solvent is chosen such as pyridine, or a base such as triethylamine may be used in conjunction with an inert solvent; and the reaction is conveniently effected at from 0° to 50° C., for example at room temperature.

The acid $R^1.OH$ is a strong acid, preferably a strong organic acid. It will be appreciated that the group $R^1$ therein is not incorporated in the vinyl compounds, and its function is to facilitate the formation of a carbon-carbon double bond in the elimination reaction (vide infra). For this purpose, the group $R^1$ should be such as to provide a leaving group $R^1O^-$ corresponding to the anion derivable from the acid $R^1.OH$. Hence, the structure of $R^1$ is not of itself critical to the performance of the reaction all that is essential is its being able to provide a suitable leaving group $R^1O^-$, which will enable elimination rather than substitution in the step (d). The acid $R^1.OH$ must of course be compatible with the other reactants used.

Acids of formula $R^1.OH$ which are particularly useful include substituted sulphonic acids of formula $R^4.SO_3H$ wherein $R^4$ is lower alkyl having 1 to 6, preferably 1 to 4 carbon atoms, aryl such as phenyl and aralkyl such as benzyl or phenethyl, wherein each of alkyl, aryl and aralkyl may have one or more substituents selected from a halogen, preferably fluoro, chloro or bromo, and a lower alkyl group; for example p-toluenesulphonic acid, trifluoromethanesulphonic acid, methanesulphonic acid, and p-bromobenzenesulphonic acid. Other useful acids of formula $R^1.OH$ are halogen-substituted alkanoic acids having 1 to 6, preferably 1 to 4 carbon atoms such as trichloroacetic acid or trifluoroacetic acid.

The olefin (VI) may be produced from the ester (V) by eliminating the leaving group $R^1O^-$ in association with a hydrogen and forming the appropriate carbon-carbon double bond. The elimination is effected in the presence of a base which preferably should be used in at least molar equivalent to the compound (V). In order to minimise the competitive substitution reaction, the conditions are chosen which favour elimination by using a strong base. Any base which is capable of abstracting hydrogen from the compound (V) may be used.

Examples of suitable reactants for the elimination step include an an alkali metal alkoxide, such as sodium methoxide or ethoxide or potassium tertiary butoxide, in the corresponding alkanol; an alkali metal hydroxide such as sodium hydroxide in an alkanol; and potassium tertiary butoxide in a non-polar solvent such as benzene or toluene or in a halogenated aliphatic hydrocarbon solvent such as carbon tetrachloride, dichloromethane or dichloroethane; the reaction may be effected at room temperature or with heating up to the reflux temperature of the reaction mixture.

When employing the synthetic route outlined in Scheme A it is of course possible to vary, if desired, the value of the radical X from one group to another within the definition given above; for example it may be convenient to effect step (a) using an alkyl ester, but thereafter to convert the compound of formula (III) to the desired ester of an alcohol B.OH before proceeding with the synthesis. Similarly it is essential that for any particular step, the radical X should be compatible with the reactants which are used.

If in the compound of formula (VI) the variable X is an ester of the desired alcohol B.OH, wherein B is as defined hereinbelow, then the resulting olefin is the required insecticidal ester of formula (I). Alternatively, the olefin (VI) may be converted to the appropriate ester by conventional techniques such as transesterification or by hydrolysis (where necessary) to the acid (VII) followed by esterification.

For example, compounds of formula (VI) wherein X is other than carboxyl may be converted into the corresponding carboxylic acid of formula (VII) by standard techniques such as acid or alkaline hydrolysis. Conveniently, using suitable conditions for the elimination reaction (vide supra) and an excess of base as appropriate, a compound of formula (V) may be converted directly to the carboxylic acid (VII) without isolation of the intermediate (VI).

The insecticidal esters of formula (I) may be prepared by esterification of the alcohol BQ or a reactive derivative thereof with the acid (VII) or a reaction derivative thereof of formula (VIII):

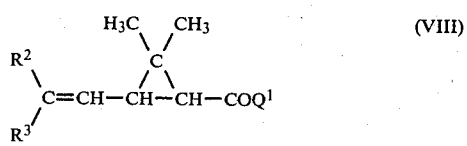

wherein $R^2$ and $R^3$ are each halo, and Q and $Q^1$ are functional groups or atoms which react together to form an ester linkage and B has the value defined hereinbelow.

Conveniently the acid (VII), its acid anhydride with chloroformic acid or its acid halide is reacted with an alcohol BOH; or a halide BHal, wherein 'Hal' represents a halide, is reacted with a salt of the acid (VII) for example an alkali metal salt such as sodium, the silver salt or triethylammonium salt; or an acid (VII) or a reactive derivative thereof such as the ammonium salt, an alkylammonium salt wherein 'alkyl' has 1 to 6 carbon atoms, or preferably an alkali metal salt such as sodium is reacted with a quaternary ammonium salt $BA^+Hal^-$ wherein A is an alkylamine or N-alkylaniline, wherein each of which 'alkyl' has 1 to 6 carbon atoms, or pyridine and $Hal^-$ is halide. The term halide means flouride, chloride, bromide or iodide, of which the chloride or bromide is to be preferred.

Alternatively an ester of formula (VI) (wherein X is a group COOM) is subjected to transesterification with an alcohol BOH by any method well known in the art of chemistry, for example using a basic catalyst such as a sodium alkoxide.

The starting acetyl compounds (II) may be made by any known method, such as that described in U.S. Pat. No. 3,397,223, for example by the reaction shown in Scheme (B) below wherein R and X have the same meaning as in formula (II).

SCHEME B

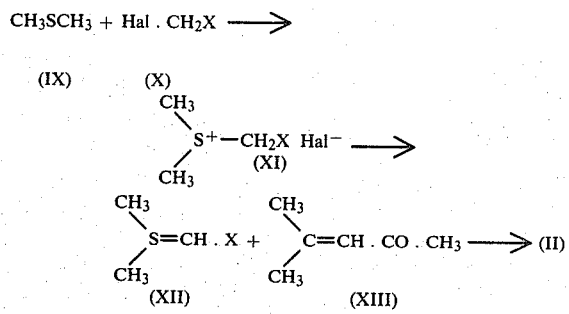

In this scheme, the compounds of formula (II) are prepared by the reaction of mesityl oxide (XIII) with a dimethylsulphuranylidene compound (XII). The latter reactant (XII) may itself be prepared from a corresponding substituted dimethylsulphonium salt (XI) obtained from compound (X) wherein 'Hal' is a halogen such as bromo, and dimethyl sulphide.

The sulphonium compound (XI) is preferably made by reaction of dimethyl sulphide with compound (X) in a polar or non-polar solvent at room temperature. The resulting sulphonium product (XI) may then be dehydrohalogenated by a base such as alkali metal hydroxide, alkoxide or hydride in an alkanol. Preferably an aqueous alkali metal carbonate solution and chloroform are used to minimise the decomposition of the ylide (XII).

Those acetyl compounds (II) which are esters of an alcohol BOH are conveniently prepared by known techniques from other corresponding acetyl compounds. For example by transesterification of the alkyl ester or hydrolysis and esterification analogous to the conversion of an olefin of formula (VI) to a compound of formula (I).

In the desired insecticidal esters of formula (I) the cyclic residue B is derived from a compound of the formula BOH wherein B is:

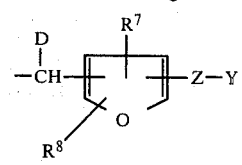

or

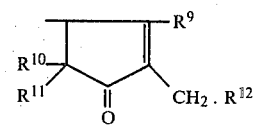

or

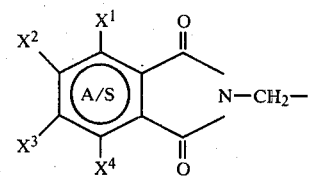

or

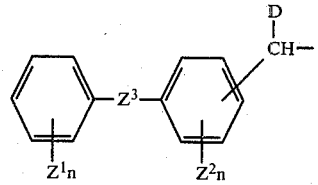

or

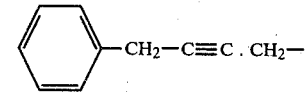

or

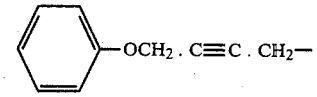

wherein
Z represents O, S, $CH_2$ or CO, Y represents hydrogen or an alkyl, alkenyl or alkynyl group or an aryl or furyl group which is unsubstituted or substituted in the ring by one or more alkyl, alkenyl, alkoxy or halogeno groups; $R^7$ and $R^8$, which may be the same or different, each represent hydrogen or an alkyl or alkenyl group;

$R^9$ represents hydrogen or a methyl group;

$R^{10}$ and $R^{11}$, which may be the same or different, each represent hydrogen or an alkyl group;

$R^{12}$ represents an organic radical having carbon-carbon unsaturation in a position α to the $CH_2$ group to which $R^{12}$ is attached;

(A/S) indicates an aromatic ring or a dihydro or tetrahydro analogue thereof;

$X^1$, $X^2$, $X^3$ and $X^4$, which may be the same or different, each represent hydrogen, chlorine or a methyl group; and $Z^3$ represents $-CH_2-$ or $-O-$ or $-S-$ or $-CO-$; D represents H, CN or $-C\equiv CH$; $Z^1$ and $Z^2$, which may be the same or different, each represent chlorine or a methyl group; and n is 0, 1 or 2.

Highly active examples of such insecticidal esters of formula (I) include those derived from 5-benzyl-3-furylmethyl alcohol (in formula (XIV): Z-Y is 5-benzyl, D=$R^7$=$R^8$ is hydrogen) and m-phenoxybenzyl alcohol (in formula (XVII): $Z^3$ is oxygen, D is hydrogen, n is 0). Other specific esters within the scope of the above classes are described in detail in British Pat. No. 1,413,491.

Synthesis of the acetyl compounds (II) by the reactions outlined in Scheme B specifically provides the desired pure trans geometrical isomers, and the subsequent reaction sequence to the vinyl esters (VI) retains the trans configuration. Nevertheless, if desired, any trans compound of formula (II) to (VII) may be converted into its cis isomer or a cis/trans mixture for the purpose of producing the cis or cis/trans insecticidal compounds of formula (I).

Conveniently a cis/trans mixture may be produced by converting a compound of formulae (II), (III), (V) or (VI) to its acid chloride, and heating the acid chloride above 100° C., for example to 110° C. to 150° C. Heating the acid chloride of the acid (VII) leads to an equilibrium mixture of 20–25: 80–75 cis/trans ratio. Alternatively the conversion to cis/trans mixtures may be effected by ultra-violet irradiation, and such mixtures may be separated by any known method including distillation of an ester (R is alkyl) or fractional crystallisation of the corresponding acids (R is hydrogen).

The intermediates of formulae (II) to (VII), as well as the insecticidal esters of formula (I) may exhibit optical as well as geometrical isomerism.

The formation of the cyclopropane ring at an early stage in the route to (VI) and (VII), permits resolution, if required, of the optical isomers of the racemate starting acetyl compounds (II) to obtain the more active insecticidal (+) isomers of compounds (I) via the (+) isomers of compounds (II) to (V).

The racemates of any of these compounds may be resolved into the (+) and (−) isomers to produce the corresponding (+) or (−) insecticidal esters, or the racemates may themselves be used to produce the racemic insecticidal esters of formula (I).

The racemates of compounds (II) to (VI) may be resolved by known methods, preferably by optical resolution of the corresponding (±) acid with an optically active base, for example an alkaloid such as quinine, or α-phenylethylamine, or threo-1-p-nitrophenyl-2-(N,N-dimethylamino)propane-1,3-diol.

Accordingly, the present invention provides the following features which we will claim but the invention is not limited thereto and includes any novel feature herein described:
(a) A compound of formula (III), (IV) and (V).
(b) A compound of formula (III), (IV) and (V) having the trans configuration.
(c) A compound of formula (III), (IV) and (V) in the form of their racemates.
(d) The synthesis of a compound of formula (III) comprising the halogenation of a compound of formula (II).
(e) The synthesis of a compound of formula (IV) comprising the reduction of a compound of formula (III).
(f) The esterification of a compound of formula (IV) with an acid $R^1OH$ to provide an ester of formula (V).
(g) The elimination of the acid $R^1OH$ from a compound of formula (V) (optionally with simultaneous hydrolysis) to provide a compound of formula (VI) (or its acid of formula (VII) respectively) and where the ester (VI) is produced, hydrolysis of said ester to acid (VII).
(h) The synthesis of a compound of formula (I) wherein B is a cyclic residue as hereinbefore defined comprising the esterification of an acid of formula (VII) or a reactive derivative thereof with an alcohol BOH or a reactive derivative thereof, said acid or reactive derivative thereof being derived from a compound of formula (V).
(i) The synthesis as defined in paragraph (h) wherein the compound of formula (V) is derived from a compound of formula (IV).
(j) The synthesis as defined in paragraph (i) above wherein the compound of formula (IV) is derived from a compound of formula (III).
(k) The synthesis as defined in paragraph (j) above wherein the compound of formula (III) is derived from a compound of formula (II).
(l) The synthesis of (±)m-phenoxybenzyl 3-(2,2-dichlorovinyl)-2,2-dimethylcyclopropane-1-carboxylate by the process described in any of paragraphs (g) to (k) above.

The following are examples of the invention.

EXAMPLE 1

A: Carboethoxymethyl Dimethylsulphonium Bromide

A solution of ethyl bromoacetate (530 g, 3.17 M) and dimethyl sulphide (228 g, 3.67 M) in acetone (1.0 l) was stirred at room temperature for three days. Filtration of the mixture yielded the sulphonium bromide as a white crystalline solid m.p. 78°–9° C.

B: Ethyl (Dimethylsulphuranylidene) Acetate

A solution of sulphonium bromide (85.7 g, 0.37 M) in chloroform (280 ml) was vigorously stirred at 5°–10° C. and treated in one portion with a mixture of saturated potassium carbonate solution (212 ml) and 12.5 N sodium hydroxide solution (29.5 ml). The reaction mixture was warmed to 15°–20° C. and was held there for 15 minutes. After removal of the salt by filtration, the filtrate was separated and the upper chloroform layer dried for 2 hours over anhydrous potassium carbonate. Removal of the solvent in vacuo at 25° C. and 1 mm mercury pressure gave the ylide as a pale yellow oil.

C: (±) Trans Ethyl 3-Acetyl-2,2-Dimethylcyclopropane-1-Carboxyl

A solution of the ylide (49.3 g, 0.33 M) and mesityl oxide (146 g, 1.49 M) in dry benzene (750 ml) was refluxed for 18 hours. Removal of the solvent and excess reagent by distillation gave a residue. This liquid was fractionally distilled and the cut boiling at 45° C. and 0.1 mm mercury pressure collected to yield the desired cyclopropane as a colourless liquid.

EXAMPLE 2

(±) Trans Ethyl 3-Dichloroacetyl-2,2-Dimethylcyclopropane-1-Carboxylate

Sulphuryl chloride (59.4 g, 0.44 M) was added dropwise to ethyl 3-acetyl-2,2-dimethylcyclopropane-1-carboxylate (20.4 g, 0.11 M) with ice cooling. The solution was stirred at room temperature for 16 hours. Excess reagent was removed under vacuum and the residue dissolved in ether (50 ml). The ether was washed with water, dried over anhydrous sodium sulphate and evaporated in vacuo to give a pale yellow liquid bp 85° C./0.05 mm/mercury.

EXAMPLE 3

(±) Trans Ethyl 3-(β,β-Dichloro-α-Hydroxyethyl)-2,2-Dimethylcyclopropane-1-Carboxylate Solid sodium borohydride (2.4 g, 0.063 M) was added portionwise to a cooled solution of (±) trans ethyl 3-dichloroacetyl-2,2-dimethylcyclopropane-1-carboxylate (16.0 g, 0.063 M) in methanol (160 ml). The reaction was stirred at room temperature for 3 hours. Most of the methanol was removed in vacuo and the residue poured into ice/water (150 ml). This was extracted with ether (3×100 ml), the ether extracts combined, dried over anhydrous sodium sulphate and evaporated in vacuo to yield the hydroxy compound as a pale yellow liquid b.p. 110° C./0.07 mm mercury.

EXAMPLE 4

(±) Trans Ethyl 3-(β,β-Dichloro-α-Hydroxyethyl)-2,2-Dimethylcyclopropane-1-Carboxylate Aluminium isopropoxide (0.97 g, 0.005 M) and (±) trans ethyl 3-dichloroacetyl-2,2-dimethylcyclopropane-1-carboxylate (1.0 g, 0.004 M) were refluxed in isopropanol (6.0 ml) for 16 hours. On cooling, the mixture was poured into 2 N hydrochloric acid (50 ml) and then extracted with ether (3×30 ml). The combined organic layers were extracted with water (2×50 ml), dried and evaporated in vacuo to yield a colourless oil. This product was identical (n.m.r. and i.r. spectra and g.l.c.) to the title product obtained from the sodium borohydride reduction described above in Example 3.

EXAMPLE 5

(±) Trans Ethyl-3-(β,β-Dichloro-α-Tosyloxyethyl)-2,2-Dimethylcyclopropane-1-Carboxylate A solution of (±) trans ethyl 3-(β,β-dichloro-α-hydroxyethyl)-2,2-dimethylcyclopropane-1-carboxylate (28.0 g, 0.11 M) in pyridine (168 ml) was added dropwise to a solution of tosyl chloride (44.2 g, 0.23 M) in pyridine (224 ml) maintained at 40° C. After the addition the mixture was stored for 3 days at 4° C. The majority of the pyridine was removed under vacuum at 40° C. and the residue was poured into ice/water (200 ml). After acidification with concentrated hydrochloric acid, this mixture was extracted with ether (3×100 ml), the ether layers combined, dried and evaporated to a pale yellow oil, which crystallised on standing. The tosylate was recrystallised from cyclohexane, m.p. 71° C.

EXAMPLE 6

(±) Trans Ethyl 3-(β,β-Dichlorovinyl)-2,2-Dimethylcyclopropane-1-Carboxylate (±) Trans ethyl 3-(β,β-dichloro-α-tosyloxyethyl)-2,2-dimethylcyclopropane-1-carboxylate (0.5 g, 0.0012 M) and N sodium hydroxide solution (2.5 ml) in ethanol (2.5 ml) were refluxed for 1 hour. On cooling the mixture was poured into water (20 ml), acidified with concentrated hydrochloric acid and extracted with ether (3×10 ml). The combined organic phases were washed with water (2×15 ml), dried over anhydrous sodium sulphate and evaporated in vacuo to yield a colourless oil. This oil was identical (n.m.r. and i.r. spectra and g.l.c.) with an authentic sample of the title ester.

EXAMPLE 7

(±) Trans 3-(β,β-Dichlorovinyl)-2,2-Dimethylcyclopropane-1-Carboxylic Acid (±) Trans ethyl 3-(β,β-dichlorovinyl)-2,2-dimethyl cyclopropane-1-carboxylate (4.2 g, 0.018 M) and N sodium hydroxide solution (36.0 ml) in ethanol (36.0 ml) were refluxed for 1 hour. On cooling, the mixture was poured into water (200 ml) and acidified with concentrated hydrochloric acid. This was extracted with ether (3×100 ml), the ether layers combined, washed with water (2×100 ml), dried over anhydrous sodium sulphate and evaporated in vacuo. An off-white solid was produced and recrystallisation was achieved from cyclohexane to yield the title acid, m.p. 94°–95° C.

EXAMPLE 8

(±) Trans 3-(β,β-Dichlorovinyl)-2,2-Dimethylcyclopropane-1-Carboxylic Acid

A mixture of (±) trans ethyl 3-(β,β-dichloro-α-tosyloxyethyl) 2,2-dimethylcyclopropane-1-carboxylate (10.0 g, 0.024 M) in ethanol (100 ml) and N sodium hydroxide solution (100 ml) were refluxed for 1 hour. Excess alcohol was removed under vacuum and the residue acidified with concentrated hydrochloric acid, and extracted with ether (3×60 ml). The combined ether layers were extracted with saturated brine (2×100 ml), dried over anhydrous sodium sulphate and evaporated in vacuo to yield the acid as a cream solid. Recrystallisation was achieved from cyclohexane m.p. 93°–5° C. (Lit. 95°–6°).

EXAMPLE 9

(±) Trans m-Phenoxybenzyl 3-(β,β-Dichlorovinyl)-2,2-Dimethylcyclopropane-1-Carboxylate (±) Trans 3-(β,β-dichlorovinyl)-2,2-dimethylcyclopropane1-carboxylic acid (1.0 g, 0.0048 M), m-phenoxybenzyl alcohol (1.0 g, 0.0050 M) and para-toluene sulphonic acid (0.01 g) in toluene (100 ml) were refluxed with a Dean and Stark take-off for 36 hours. On cooling, the solution was extracted with 5% aqueous sodium bicarbonate (2×50 ml), then water (2×50 ml), dried over anhydrous sodium sulphate and evaporated in vacuo. The residue was passed down an acid washed alumina column using petroleum ether (b.p. 80°–100° C.) as eluant. On evaporation of the solvent, this yielded a colourless oil which crystallised on standing. The product was identical (n.m.r., i.r. and u.v. spectra, t.l.c. and g.l.c.) to an authentic sample of the title ester.

EXAMPLE 10

A: (±) Trans Ethyl 3-(β,β-dichloro-α-brosyloxyethyl)-2-dimethylcyclopropane-1-carboxylate A solution of (±) trans ethyl 3-(β,β-dichloro-α-hydroxyethyl)-2,2-dimethylcyclopropane-1-carboxylate (5.0 g, 0.020 m) in pyridine (30 ml) was added dropwise to a solution of brosyl chloride (10.18 g, 0.040 m) in pyridine (30 ml) maintained at 40° C. After the addition the mixture was stirred at room temperature for 3 days and then poured into water (200 ml), acidified with concentrated hydrochloric acid, extracted with ether (3×80 ml), dried over anhydrous magnesium sulphate and evaporated in vacuo to give a white solid. This was recrystallised from cyclohexane m.p. 83° C.

B: By a similar reaction wherein the brosyl chloride is replaced by mesyl chloride was prepared (±) trans ethyl 3-($\beta,\beta$-dichloro-$\alpha$-mesyloxyethyl)-2,2-dimethyl-cyclopropane-1-carboxylate, which is a pale yellow liquid.

$\delta(CDCl_3)$ 1.12–1.39(9H,m), 1.62–2.15(2H,m), 3.18(3H,s), 4.18(2H,q,J 7 Hz), 4.70(1H, d of d,J 3 & 9 Hz), 6.03 (1H,d,J 3 Hz).

EXAMPLE 11

(±) Trans Ethyl 3-($\beta,\beta$-dichlorovinyl)-2,2-dimethylcyclopropane-1-carboxylate A: A mixture of the brosylate product of Example 10A (1.3 g, 0.0027 m) in ethanol (5.4 ml) and N sodium hydroxide solution (5.4 ml) was refluxed for 1 hour. After cooling the reaction mixture was poured into water (100 ml) and acidified with concentrated hydrochloric acid. This was extracted with ether (3×50 ml), dried over anhydrous magnesium sulphate and evaporated in vacuo to yield the product as a colourless oil.

B: The mesylate product of Example 10B was converted to the title compound in like manner.

EXAMPLE 12

(±) Trans Ethyl 3-($\beta,\beta$-dichloro-$\alpha$-trifluoroacetoxyethyl)-2,2-dimethyl-cyclopropane-1-carboxylate (±) Trans ethyl 3-($\beta,\beta$-dichloro-$\alpha$-hydroxyethyl)-2,2-dimethylcyclopropane-1-carboxylate (1.0 g, 0.004 m) was treated with trifluoroacetic anhydride (5.0 g, 0.024 m) and the mixture stirred at room temperature for 16 hours, in a moisture free atmosphere. Excess reagent was removed in vacuo, leaving the trifluoroacetate as a pale yellow liquid. This was stored in the absence of moisture and used without further purification.

$\delta(CDCl_3)$ 1.08–1.41(9 Hz,m), 1.57–2.07(2H,m), 4.18(2H,q,J7 Hz), 5.06 (1H,d, of d,J5 & 9 Hz), 5.92(1H,d,J5 Hz).

EXAMPLE 13

(±) Trans Ethyl 3-($\beta,\beta$-dichlorovinyl)-2,2-dimethylcyclopropane-1-carboxylate The trifluoroacetate product of Example 12 (2.0 g, 0.0057 m) in dry benzene (15 ml) was treated with potassium tertiary butoxide (0.96 g, 0.0086 m) and the mixture stirred at room temperature for 20 hours. This was evaporated in vacuo and the residue extracted with 40/60 petroleum ether. After filtration the petrol was evaporated in vacuo and the residue separated by g.l.c.

EXAMPLE 14

Trans 3-Acetyl-2,2-dimethylcyclopropane-1-carboxylic acid

Ethyl 3-acetyl-2,2-dimethylcyclopropane-1-carboxylate (36.0 g, 0.2 m) and N potassium hydroxide (391 ml) in ethanol (391 ml) was refluxed for two hours. Excess alcohol was removed in vacuo and the resulting solution acidified with concentrated hydrochloric acid ($\approx$40 ml). This precipitated a solid which was extracted with ether (3×200 ml), the ether dried over anhydrous MgSO$_4$ and evaporated in vacuo to give a cream solid m.p. 111° C.

EXAMPLE 15

(±) Trans 3-Acetyl-2,2-dimethylcyclopropane-1-carboxamide

Thionyl chloride (45.7 g, 0.40 m) was added dropwise to a solution of 3-acetyl-2,2-dimethylcyclopropane-1-carboxylic acid (30.0 g, 0.20 m) in benzene (300 ml) and the mixture refluxed for two hours. Excess solvent and reagent were removed in vacuo and the residue dissolved in dimethoxyethane (320 ml). This solution was added to dimethoxyethane (1600 ml) which had been saturated with ammonia gas and the mixture stood at room temperature for 16 hours. After removal of some inorganic salts by filtration, the filtrate was evaporated in vacuo to give a white solid which was identified as the required amide.

EXAMPLE 16

(±) Trans 3-Acetyl-1-cyano-2,2-dimethylcyclopropane

Phosphorus oxychloride (202.4 g, 1.32 m) was added dropwise to a solution of 3-acetyl-2,2-dimethyl-cyclopropane-1-carboxamide. (34.6 g, 0.22 m) in benzene (140 ml) and the resultant mixture refluxed for 3 hours. Excess reagents were removed in vacuo and the residue dissolved in ether (100 ml). The ether was washed with water (3×60 ml), dried over anhydrous magnesium sulphate and evaporated in vacuo to give a dark oil b.p. 72°–5° C./1.0 mm.

EXAMPLE 17

(±) Trans Benzyl 3-Acetyl-2,2-dimethylcyclopropane-1-carboxylate

Thionyl chloride (25.5 g, 0.21 m) was added dropwise to a solution of 3-acetyl-2,2-dimethylcyclopropane-1-carboxylic acid (16.7 g, 0.11 m) in dry benzene (250 ml) and then refluxed for 2 hours. This mixture was evaporated in vacuo, the residue taken up in benzene (100 ml) and re-evaporated. This residue was dissolved in benzene (150 ml) and benzyl alcohol (13.1 g, 0.12 m) added. After cooling the mixture in ice, pyridine (11.3 g, 0.12 m) was added dropwise and the mixture stirred at room temperature for 16 hours. This organic phase was extracted with 2 N sodium hydroxide solution (2×80 ml), water (2×80 ml), N hydrochloric acid (2×80 ml), water (2×80 ml), and brine (1×80 ml), then dried over anhydrous magnesium sulphate and evaporated in vacuo to yield a pale yellow oil. Purification was effected by running down an alumina column (75 g) using 40/60 petroleum ether as eluent and this produced a clear viscous oil.

EXAMPLE 18

(±) Trans Benzyl 3-Dichloroacetyl-2,2-dimethylcyclopropane-1-carboxylate

Sulphuryl chloride (39.5 g, 0.29 m) was added dropwise to benzyl 3-acetyl-2,2-dimethylcyclopropane-1-carboxylate (18.0 g, 0.07 m) with ice cooling. This solution was stirred at room temperature for 16 hours. Excess reagent was removed under vacuum and the residue dissolved in ether (100 ml). The ether was washed with water (2×50 ml), dried over anhydrous magnesium sulphate and evaporated in vacuo to give a viscous oil.

δ(CDCl$_3$) 1.38(3H,s), 1.58(3H,s), 2.74(1H,d,J6 Hz), 3.17(1H,d,J6 Hz), 5.41(2H,s), 6.11(1H,s), 7.69(5H,s).

EXAMPLE 19

(±) Trans Benzyl 3-(β,β-Dichloro-α-hydroxyethyl)-2,2-dimethylcyclopropane-1-carboxylate Solid sodium borohydride (2.56 g, 0.068 m) was added portionwise to a cooled solution of the product of Example 18 (21.3 g, 0.068 m) in methanol (200 ml). The reaction was stirred for 3 hours at room temperature and then most of the methanol was removed under vacuum. The residue was poured into ice/water (200 ml) and extracted with ether (3×100 ml). The combined organic layers were dried over anhydrous magnesium sulphate and evaporated in vacuo to yield a yellow oil. Purification was effected by running down a grade III alumina column (100 g) using 40/60 petroleum ether as eluent to remove a fast running by-product. Then further elution with toluene gave the required dichloro alcohol.

δ(CDCl$_3$) 1.32(6H,s), 1.52-1.91(2H,m), 2.62(1H, broad s, exchangeable with D$_2$O), 3.51-3.79(1H,m) 5.79(1H,d,J4 Hz), 7.44(5H,s).

νmax (film) 3457, 1730, 1165, 1117, 791, 733, 698 cm$^{-1}$.

EXAMPLE 20

(±) Trans Benzyl 3-(β,β-Dichloro-α-tosyloxyethyl)-2,2-dimethylcyclopropane-1-carboxylate A solution of the product of Example 19 (5.0 g, 0.016 m) in pyridine (30 ml) was added dropwise to a solution of tosyl chloride (6.0 g, 0.032 m) in pyridine (30 ml) and the mixture allowed to stand for 3 days at room temperature. Most of the pyridine was removed under vacuum and the residue was poured into ice/water (200 ml). This was acidified with concentrated hydrochloric acid and extracted with ether (3×100 ml). The combined ether layers were dried over anhydrous magnesium sulphate and evaporated in vacuo to give a thick oil. This was triturated with 40/60 petroleum ether to yield the tosylate as an off-white solid. Recrystallisation was achieved from 60/80 petroleum ether mp 98° C.

δ(CDCl$_3$) 1.21(3H,s), 1.24(3H,s), 1.76-2.22(2H,m), 2.52(3H,s), 4.72(1H,d of d, J 3 & 9 Hz), 5.22(2H,s), 5.99(1H,d,J3 Hz), 7.26-7.95(9H,m).

νmax (mull) 1726, 1217, 1177, 920, 840 cm$^{-1}$.

EXAMPLE 21

(±) Trans Benzyl 3-(β,β-Dichlorovinyl)-2,2-dimethylcyclopropane-1-carboxylate

Potassium tertiary butoxide (0.74 g, 0.0066 m) was added to the product of Example 18 (2.0 g, 0.0044 m) in dry benzene (100 ml) and the mixture refluxed for 16 hours. On cooling, the reaction was poured into ice/water (200 ml) and acidified with concentrated hydrochloric acid. The organic layer was separated and the aqueous layer extracted with ether (2×100 ml). The combined organic layers were dried over anhydrous magnesium sulphate and evaporated in vacuo to yield a brown oil. This was purified by running down a grade III alumina column (6 g) using 60/80 petroleum ether as eluent and this yielded the desired compound as a colourless oil. This product was identical (n.m.r. and i.r. spectra, t.l.c. and g.l.c.) with an authentic sample.

δ(CDCl$_3$) 1.18(3H,s), 1.34(3H,s), 1.67(1H,d,J6 Hz), 2.29(1H,d of d, J 6 & 9 Hz), 5.18(2H,s), 5.67(1H,d,J9 Hz), 7.42(5H,s).

νmax (film) 1731, 1225, 1166, 1117, 882, 698 cm$^{-1}$.

EXAMPLE 22

Meta Phenoxybenzyl (Dimethylsulphuranylidene) Acetate

A solution of carbo-(meta-phenoxybenzoxy)methyl dimethylsulphonium bromide (50.0 g, 0.13 m) in chloroform (103 ml) was vigorously stirred at 5°-10° C. and treated, in one portion, with a mixture of saturated potassium carbonate solution (78 ml) and 12.5 N sodium hydroxide solution (10.3 ml). The reaction mixture was warmed to 15°-20° C. and was held there for 15 minutes. After removal of the salt by filtration, the filtrate was separated and the upper chloroform layer dried for 2 hours over anhydrous potassium carbonate. Removal of the solvent in vacuo at 25° C. and 1 mm pressure gave the yield as a pale yellow oil.

EXAMPLE 23

(±) Trans meta-Phenoxybenzyl 3-Acetyl-2,2-dimethylcyclopropane-1-carboxylate (a) A solution of the product of Example 22 (34.6 g, 0.11 m) and mesityl oxide (44.7 g, 0.46 m) in ethanol (330 ml) was refluxed for 16 hours. Removal of the solvent and excess reagent in vacuo gave a residue of 37.5 g. This was purified by running down a grade III alumina column (120 g) using 60/80 petroleum ether containing 10% toluene as eluent and this yielded the desired compound as a pale yellow oil.

(b) A solution of (±) trans 3-acetyl-2,2-dimethylcyclopropane-1-carboxylic acid (33.3 g, 0.21 m) in dry benzene (500 ml) was treated with thionyl chloride (50.8 g, 0.42 m) and refluxed for 2 hours. This was evaporated in vacuo to remove all excess reagents and the residue was dissolved in dry benzene (300 ml). Meta phenoxybenzyl alcohol (38.3 g, 0.21 m) was added followed by dropwise addition of pyridine (16.8 g, 0.21 m) to the cooled solution. The reaction was stirred at room temperature for 16 hours. After filtration, the solution was extracted with 2 N sodium hydroxide solution (2×100 ml), water (2×100 ml), N hydrochloric acid (2×100 ml), water (2×100 ml) and saturated brine (1×100 ml), then dried over anhydrous magnesium sulphate and finally evaporated in vacuo to yield the ester. This product was identical (i.r. and n.m.r. spectra, t.l.c. and g.l.c.) to that prepared via the sulphur yield above.

EXAMPLE 24

(±) Trans meta Phenoxybenzyl 3-Dichloroacetyl-2,2-dimethylcyclopropane-1-carboxylate (a) Chlorine gas (2.1 g, 0.03 m) was dissolved in ice cooled carbon tetrachloride (50 ml) and to this solution was added m-phenoxybenzyl 3-acetyl-2,2-dimethylcyclopropane-1-carboxylate (1.3 g, 0.004 m). The flask was stoppered and stood at room temperature for 16 hours. Removal of the solvent in vacuo left a pale yellow oil. This material was purified by chromatography on a grade III alumina column (8 g) using 40/60 petroleum ether as eluent and the slowest running compound was collected. Spectroscopic identification of this compound showed it to be the desired compound.

δ(CDCl$_3$) 1.29(3H,s), 1.48(3H,s), 2.59(1H,d, J 5 Hz), 3.02(1H,d,J 5 Hz), 4.73(2H,s), 5.22(1H,s), 5.22(1H,s) 6.96–7.61(9H,m).

(b) A solution of 3-dichloroacetyl-2,2-dimethylcyclopropane-1-carboxylic acid (1.0 g, 0.004 m) in dry benzene (25 ml) was treated with thionyl chloride (1.2 g, 0.008 m) and refluxed for 2 hours. This was evaporated in vacuo to remove all excess reagents and the residue dissolved in dry benzene (25 ml). Meta phenoxybenzyl alcohol (0.8 g, 0.004 m) was added, the mixture cooled in ice and pyridine (0.4 g, 0.005 m) added dropwise. The reaction was stirred at room temperature for 16 hours. After filtration, the solution was extracted with 2 N sodium hydroxide solution (2×20 ml), water (2×20 ml), N hydrochloric acid (2×20 ml), water (2×20 ml) and saturated brine (1×20 ml), then dried over anhydrous magnesium sulphate and finally evaporated in vacuo to give the ester. This product, a pale yellow oil, was identical (i.r. and n.m.r. spectra, t.l.c. and g.l.c.) to the material prepared above.

EXAMPLE 25

(±) Trans meta-Phenoxybenzyl 3-(β,β-dichloro-α-hydroxyethyl)-2,2-dimethylcyclopropane-1-carboxylate Sodium borohydride (3.17 g, 0.084 m) was added portionwise to a cooled solution of the product of Example 24 (34.0 g, 0.084 m) in methanol (300 ml). The reaction was stirred for 3 hours at room temperature and then most of the methanol was removed in vacuo, before pouring the residue into ice/water (300 ml). This was extracted with ether (3×150 ml), the combined ether layers dried over anhydrous magnesium sulphate and the ether finally evaporated to yield a viscous oil. Purification was effected by running down a grade III alumina column (150 g) using 60/80 petroleum ether as eluent to remove a fast running by-product. Then further elution with 60/80 petroleum ether containing 10% toluene gave the required dichloro alcohol.

δ(CDCl$_3$) 1.39(6H,s), 1.69–1.94(2H,m), 2.63(1H,s, exchangeable with D$_2$O), 3.54–3.83(1H,m), 5.20(2H,s), 5.81(1H,d,J5 Hz), 6.99–7.56(9H,m).

ν$_{max}$ (film) 3462, 1732, 1589, 1490, 1258, 1216, 1165, 692 cm$^{-1}$.

EXAMPLE 26

(±) Trans meta-Phenoxybenzyl 3-(β,β-dichloro-α-tosyloxyethyl)-2,2-dimethylcyclopropane-1-carboxylate A solution of the product of Example 25 (12.5 g, 0.03 m) in pyridine (50 ml) was added dropwise to a solution of tosyl chloride (12.1 g, 0.063 m) in pyridine (50 ml) and the mixture allowed to stand for 3 days at room temperature. Most of the pyridine was removed in vacuo and the residue poured into ice/water (300 ml). This was acidified with concentrated hydrochloric acid and extracted with ether (3×150 ml). The combined ether layers were dried over anhydrous magnesium sulphate and evaporated in vacuo to give a viscous oil. This oil was purified by elution through a grade III alumina column (50 g) using 40/60 petroleum ether.

δ(CDCl$_3$) 0.94(3H,s), 1.08(3H,s), 1.38–1.90(2H,m), 2.23(3H,s), 4.49(1H,d of d,J3 & 9 Hz), 4.96(2H,s), 5.92(1H,d,J3 Hz), 6.75–7.81(13H,m).

ν$_{max}$ (film) 1732, 1590, 1491, 1258, 1216, 1178, 692 cm$^{-1}$.

EXAMPLE 27

(±) Trans meta-Phenoxybenzyl 3-(β,β-dichlorovinyl)-2,2-dimethylcyclopropane-1-carboxylate Potassium tertiary butoxide (0.45 g, 0.004 m) was added to the product of Example 26 (1.0 g, 0.002 m) in dry benzene (20 ml) and the mixture refluxed for 16 hours. On cooling the reaction was poured into ice/water (100 ml) and acidified with concentrated hydrochloric acid. The organic layer was separated and the aqueous layer extracted with ether (2×50 ml). The combined organic layers were dried over anhydrous magnesium sulphate and evaporated in vacuo to give a yellow oil. Purification was effected by chromatography on a grade III alumina column (3 g) eluting with 40/60 petroleum ether to produce a white solid m.p. 45° C. This product was identical (i.r. and n.m.r. spectra and t.l.c. and g.l.c.) to authentic material.

EXAMPLE 28

(±) Trans Ethyl 3-dibromoacetyl-2,2-dimethylcyclopropane-1-carboxylate

Bromine (26.0 g, 0.160 m) was added dropwise to ethyl 3-acetyl-2,2-dimethylcyclopropane-1-carboxylate (12.0 g, 0.065 m) in ether (600 ml). The solution was extracted with 10% sodium bicarbonate solution (3×200 ml) and water (2×200 ml), dried over anhydrous magnesium sulphate and evaporated in vacuo to yield a pale yellow liquid. No further purification was attempted with this compound.

EXAMPLE 29

(±) Trans Ethyl 3-(β,β-dibromo-α-hydroxyethyl)-2,2-dimethylcyclopropane-1-carboxylate Solid sodium borohydride (2.38 g, 0.063 m) was added portionwise to a cooled solution of the dibromo ketone product of Example (21.6 g, 0.063 m) in methanol (300 ml). The reaction was stirred at room temperature for 3 hours. Most of the methanol was removed in vacuo and the residue poured into ice/water (200 ml). This was extracted with ether (3×100 ml), the ether combined, dried over anhydrous magnesium sulphate and evaporated in vacuo to yield the hydroxy compound as a pale yellow oil b.p. 130° C./0.1 mm.

EXAMPLE 30

(±) Trans Ethyl 3-(β,β-Dibromo-α-tosyloxyethyl)-2,2-dimethylcyclopropane-1-carboxylate A solution of the product of Example 29 (11.0 g, 0.032 m) in pyridine (63 ml) was added dropwise to a solution of tosyl chloride (12.7 g, 0.067 m) in pyridine (92 ml) and the mixture allowed to stand for 3 days at room temperature. The majority of the pyridine was removed under vacuum and the residue poured into ice/water (100 ml). After acidification, with concentrated hydrochloric acid, the mixture was extracted with ether (3×50 ml), the ether layers were combined, washed with water (3×50 ml), then brine (1×100 ml), dried over anhydrous magnesium sulphate and evaporated in vacuo to yield a pale yellow oil (15.1 g). This oil was taken up in petroleum ether (600 ml) and on standing the tosylate crystallised out as white prisms. Recrystallisation was achieved from 40/60 petroleum ether m.p. 84° C.

EXAMPLE 31

(±) Trans 3-(β,β-Dibromovinyl)-2,2-dimethylcyclopropane-1-carboxylic acid

A mixture of the product of Example 30 (3.7 g, 0.0074 m) in ethanol (30 ml) and N sodium hydroxide solution (29.6 ml) were refluxed for 3 hours. Excess alcohol was removed under vacuum and the residue was acidified with concentrated hydrochloric acid. On standing a pale yellow precipitate was deposited which was filtered off, washed with water and dried. Recrystallisation was achieved from 40/60 petroleum ether m.p. 125°–6° C.

EXAMPLE 32—RESOLUTION

Trans 3-Acetyl-2,2-dimethylcyclopropane-1-carboxylic acid (±) Trans 3-Acetyl-2,2-dimethylcyclopropane-1-carboxylic acid (4.0 g, 0.026 m) was dissolved in a mixture of diisopropyl ether (170 ml) and methanol (30 ml). This solution was warmed to 60° C. and (±) α-methylbenzylamine (3.1 g, 0.026 m) added. The mixture was refluxed for 30 minutes and then cooled. The resulting crystals were removed by filtration and recrystallised twice from a mixture of diisopropyl ether and methanol (80:10). This gave a solid (2.3 g) with constant specific rotation of +10.12°. Hydrolysis of this salt with 2 N hydrochloric acid (30 ml), extraction into ether (2×20 ml), drying of the ether layers over anhydrous magnesium sulphate and final evaporation in vacuo gave the (±) acid (1.1 g, 54% yield). Recrystallisation was achieved from ethanol. N.m.r. analysis of the product using Eu(hfc)$_3$ showed the optical purity to be 62% (±) and 38% (−).

EXAMPLE 33

(±) Trans 3-Dichloroacetyl-2,2-dimethylcyclopropane-1-carboxylic acid

Sulphuryl chloride (69.1 g, 0.51 m) was added dropwise to (±) trans 3-acetyl-2,2-dimethylcyclopropane-1-carboxylic acid (10.0 g, 0.064 m) in ether (100 ml) with ice cooling. The solution was stirred at room temperature for 16 hours. Excess reagent and solvent were removed in vacuo and the residue dissolved in ether (100 ml). The ether was washed with water, dried over anhydrous magnesium sulphate and evaporated in vacuo to give a pale yellow liquid b.p. 130° C./0.7 mm.

EXAMPLE 34

Isomerisation of (±) Trans 3-Acetyl-2,2-dimethyl-cyclopropane-1-carboxylic Acid (±) Trans 3-Acetyl-2,2-dimethylcyclopropane-1-carboxylic acid (2.0 g, 0.013 m) and thionyl chloride (3.28 g, 0.026 m) in toluene (10 ml) were refluxed for one hour. Excess reagent and solvent were removed in vacuo and the residual acid chloride heated at 144° C. for seven hours. On cooling, the mixture was neutralised with 2 N sodium hydroxide solution then acidified with concentrated hydrochloric acid. This was extracted with ether (3×30 ml), the ether dried over anhydrous magnesium sulphate and evaporated in vacuo to yield a white solid (1.9 g, yield 95%). H.P.L.C. on an o.d.s. column showed presence of cis isomer (approximate ratio 70/30 trans/cis) and n.m.r. of product was identical to the trans isomer.

What we claim is:

1. A compound of formula (V)

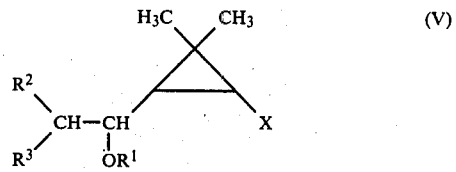

wherein $R^1$ is the radical derived from a strong organic acid of Formula $R^1$.OH, $R^2$ and $R^3$ are the same and are both either Chloro or Bromo and X is nitrile, carboxyl, carbonamide, carbonamide substituted by one or two lower alkyl groups each having 1 to 4 carbon atoms, carbonyl chloride, carbonyl bromide or a group —COOM wherein M is lower alkyl having 1 to 6 carbon atoms, phenylalkyl where alkyl has 1 to 3 carbon atoms, or a group B selected from:

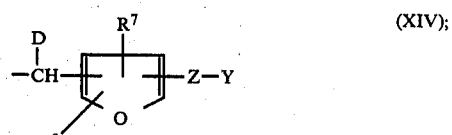 (XIV);

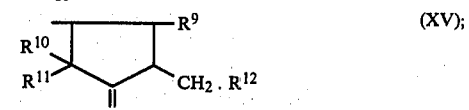 (XV);

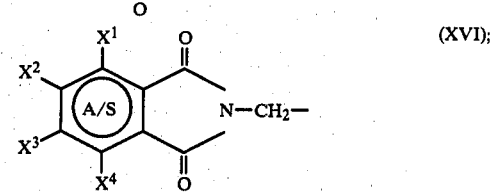 (XVI);

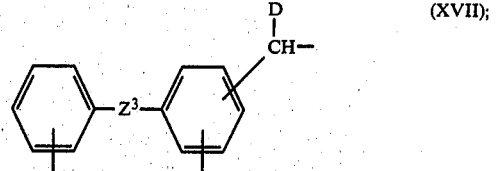 (XVII);

 (XVIII);

and

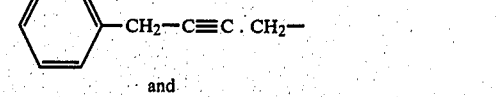 (XIX);

wherein

Z represents O, S, CH$_2$ or CO, Y represents hydrogen or an alkyl, alkenyl, or alkynyl group or an aryl or furyl group which is unsubstituted or substituted in the ring by one or more alkyl, alkenyl, alkoxy or halogeno groups; $R^7$ and $R^8$, which may be the same or different, each represent hydrogen or an alkyl or alkenyl group;

$R^9$ represents hydrogen or a methyl group;

$R^{10}$ and $R^{11}$, which may be the same or different, each represent hydrogen or an alkyl group;

$R^{12}$ represents an organic radical having carbon-carbon unsaturation in a position $\alpha$ to the $CH_2$ group to which $R^{12}$ is attached;

(A/S) indicates an aromatic ring or a dihydro or tetrahydro analogue thereof;

$X^1$, $X^2$, $X^3$ and $X^4$, which may be the same or different, each represent hydrogen, chlorine or a methyl group; and $Z^3$ represents —$CH_2$— or —O— or —S— or —CO—; D represents H, CN or —C≡CH; $Z^1$ and $Z^2$, which may be the same or different, each represent chlorine or a methyl group; and n is 0, 1 or 2.

2. The compound which is selected from the group consisting of:

($\pm$) trans ethyl 3-($\beta,\beta$-dichloro-$\alpha$-tosyloxyethyl)-2,2-dimethylcyclopropane-1-carboxylate;

($\pm$) trans ethyl 3-($\beta,\beta$-dichloro-$\alpha$-brosyloxyethyl)-2,2-dimethylcyclopropane-1-carboxylate;

($\pm$) trans ethyl 3-($\beta,\beta$-dichloro-$\alpha$-trifluoroacetoxyethyl)-2,2-dimethylcyclopropane-1-carboxylate;

($\pm$) trans benzyl 3-($\beta,\beta$-dichloro-$\alpha$-tosyloxyethyl)-2,2-dimethylcyclopropane-1-carboxylate; and ($\pm$) trans ethyl 3-($\beta,\beta$-dibromo-$\alpha$-tosyloxyethyl)-2,2-dimethylcyclopropane-1-carboxylate.

3. ($\pm$) trans m-phenoxybenzyl 3-($\beta,\beta$-dichloro-$\alpha$-tosyloxyethyl)-2,2-dimethylcyclopropane-1-carboxylate.

4. ($\pm$) trans ethyl 3-($\beta,\beta$-dichloro-$\alpha$-tosyloxyethyl)-2,2-dimethylcyclopropane-1-carboxylate.

* * * * *